(12) United States Patent
Murphy et al.

(10) Patent No.: US 7,399,887 B1
(45) Date of Patent: Jul. 15, 2008

(54) FLUORINATED SULFONATE SURFACTANTS

(75) Inventors: Peter Michael Murphy, Chadds Ford, PA (US); Andrew Edward Feiring, Wilmington, DE (US); Stephan James McLain, Wilmington, DE (US); Jessica Sinks, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/890,374

(22) Filed: Aug. 6, 2007

(51) Int. Cl.
*C07C 321/00* (2006.01)
*C07C 323/00* (2006.01)
*C07C 381/00* (2006.01)

(52) U.S. Cl. .......................... 568/22; 568/18; 568/300; 568/579

(58) Field of Classification Search .................. 568/18, 568/22, 300, 579
See application file for complete search history.

(56) References Cited

U.S. PATENT DOCUMENTS

| | | | |
|---|---|---|---|
| 3,453,333 A | 7/1969 | Litt et al. | |
| 3,547,861 A | 12/1970 | Anello et al. | |
| 4,089,804 A | 5/1978 | Falk | |
| 4,098,811 A | 7/1978 | Falk | |
| 4,171,282 A | 10/1979 | Mueller | |
| 4,460,791 A | 7/1984 | Cooke | |
| 4,877,815 A | 10/1989 | Buckmaster et al. | |
| 4,993,448 A | 2/1991 | Karydas et al. | |
| 5,023,279 A * | 6/1991 | Buckmaster et al. | 521/85 |
| 5,668,233 A * | 9/1997 | Feiring et al. | 526/247 |
| 6,664,329 B2 | 12/2003 | Gwin et al. | |
| 6,727,309 B1 | 4/2004 | Paiva et al. | |
| 6,919,173 B2 | 7/2005 | Tsionsky et al. | |
| 6,989,035 B2 | 1/2006 | Scheper et al. | |
| 7,087,710 B2 | 8/2006 | Medsker et al. | |
| 7,144,431 B2 | 12/2006 | Gardner et al. | |
| 7,164,041 B1 | 1/2007 | Moore et al. | |
| 2003/0181572 A1 | 9/2003 | Tan et al. | |
| 2005/0096244 A1 | 5/2005 | Andenaert et al. | |
| 2007/0004938 A1 | 1/2007 | Guerra | |

FOREIGN PATENT DOCUMENTS

| | | |
|---|---|---|
| BE | 861660 | 3/1978 |
| GB | 1 337 467 | 11/1973 |
| JP | 55157691 | 12/1980 |
| JP | 55158065 | 12/1980 |
| JP | 58038569 | 3/1983 |
| JP | 58038571 | * 3/1983 |
| WO | WO 2005/085187 | 9/2005 |

* cited by examiner

*Primary Examiner*—Yvonne Eyler
*Assistant Examiner*—Chukwuma O Nwaonicha

(57) ABSTRACT

A compound comprising Formula I, or a mixture thereof,

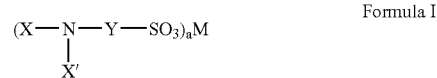

Formula I wherein
  Y is a bond or $C_mH_{2m-p}(OA)_p$ wherein m is 0 to 4, and p is 0 or 1,
  X' is X or H,
  X is $CH_2CH_2OA$, $CH(CH_2OA)_2$, $C(CH_2OA)_3$, or
  X and X' combine to form $(CH_2CH_2)_2NCH_2CH_2OA$ or $(CH_2CH_2)_2O$, provided that when X and X' combine to form $(CH_2CH_2)_2O$ then Y is $CH_2CH(OA)CH_2$,
  A is $CF_2CFHO$—$R_f$ or H,
  $R_f$ is $C_nF_{2n+1}$ wherein n is an integer of 1 to about 6,
  M is a cation having a charge equal to a, and
  a is a positive integer equal to 1 or 2,
  provided that at least one of X, X', or Y contains A equal to $CF2CFHO$—$R_f$,
and its use in lowering surface tension and imparting improved surface effects.

20 Claims, No Drawings

FLUORINATED SULFONATE SURFACTANTS

FIELD OF THE INVENTION

The present invention relates to compositions comprising fluorinated sulfonate surfactants useful for lowering surface tension and imparting improved surface effects.

BACKGROUND OF THE INVENTION

Most commercially available fluorinated surfactants are produced through electrochemical fluorination, telomerization, and oligomerization. Electrochemical fluorination utilizes anhydrous hydrofluoric acid as the fluorine source. However, industrially produced hydrofluoric acid contains impurities, which requires further complicated methods to remove these impurities.

Telomerization or oligomerization processes use tetrafluoroethylene as the starting material. However, the source of available tetrafluoroethylene is limited. The product obtained from telomerization process usually contains a mixture of homologues having different carbon chain lengths resulting in a distribution of carbon chain lengths. Therefore, the sequential separation of telomerization products is required in order to produce fluorosurfactants which contain a fixed length of the fluorinated carbon chain, as described by Erik Kissa in "Fluorinated Surfactants, Synthesis-Properties-Applications" Surfactant Science Series, Vol. 50, Marcel Dekker, New York, (1994).

U.S. Pat. No. 5,023,279 discloses the use of a special class of sulfonic and phosphonic acids, and salts of the acids to give improved nucleation for foam extrusion of thermoplastics to produce foam. The nucleating agent is of the formula $[Z(CF_2)_x(CF_2CFX)_p(R')_y(CH_2)_zRO_3]_nM$, wherein X is H, F, Cl, or $CF_3$; M is a cation; R is sulfur or phosphorus; and R' is a $C_5$-$C_6$ perfluorinated alicyclic ring diradical, a $C_1$-$C_{16}$ perfluorinated aliphatic polyether diradical with repeat units selected from $[CF_2O]$, $[CF_2CF_2O]$, and $[CF_2CF(CF_3)O]$, or a substituted or unsubstituted aromatic diradical, in which case, Z is H. The above nucleating compound is structurally different and is produced differently from the composition of the present invention.

It is desirable to have a composition comprising fluorinated surfactants which can be produced from starting materials other than tetrafluoroethylene. It is also desirable to have a method to lower surface tension using a very low concentration of surfactant and to provide surface effects. The present invention provides such a composition comprising fluorinated sulfonate surfactants which are produced from fluoroalkyl vinyl ether as the starting material for the fluorine source. The present invention also provides methods of providing various surface effects to liquids.

SUMMARY OF THE INVENTION

The present invention comprises a compound comprising Formula I, or a mixture thereof,

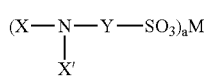
Formula I wherein
Y is a bond or $C_mH_{2m-p}(OA)_p$ wherein m is 0 to 4, and p is 0 or 1,
X' is X or H,
X is $CH_2CH_2OA$, $CH(CH_2OA)_2$, $C(CH_2OA)_3$, or
X and X' combine to form $(CH_2CH_2)_2NCH_2CH_2OA$ or $(CH_2CH_2)_2O$, provided that when X and X' combine to form $(CH_2CH_2)_2O$ then Y is $CH_2CH(OA)CH_2$,
A is $CF_2CFHO$—$R_f$ or H,
$R_f$ is $C_nF_{2n+1}$ wherein n is an integer of 1 to about 6,
M is a cation having a charge equal to a, and
a is a positive integer equal to 1 or 2.
provided that at least one of X, X', or Y contains A equal to $CF2CFHO$—$R_f$.

The present invention further comprises a method of altering the surface behavior of a liquid comprising adding to the liquid a compound of Formula I, or a mixture thereof.

DETAILED DESCRIPTION OF THE INVENTION

All trademarks are denoted herein by capitalization. All patents and patent applications cited herein are hereby incorporated by reference.

The present invention comprises a compound comprising formula I

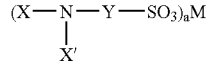
Formula I wherein
Y is a bond or $C_mH_{2m-p}(OA)_p$ wherein m is 0 to 4, and p is 0 or 1,
X' is X or H,
X is $CH_2CH_2OA$, $CH(CH_2OA)_2$, $C(CH_2OA)_3$, or
X and X' combine to form $(CH_2CH_2)_2NCH_2CH_2OA$ or $(CH_2CH_2)_2O$, provided that when X and X' combine to form $(CH_2CH_2)_2O$ then Y is $CH_2CH(OA)CH_2$,
A is $CF_2CFHO$—$R_f$ or H,
$R_f$ is $C_nF_{2n+1}$ wherein n is an integer of 1 to about 6,
M is a cation having a charge equal to a, and
a is a positive integer equal to 1 or 2,
provided that at least one of X, X', or Y contains A equal to $CF_2CFHO$—$R_f$.

In Formula I, $R_f$ is a straight or branched perfluoroalkyl group having about from 1 to about 6 carbon atoms, preferably having from about 3 to about 4 carbon atoms. M is preferably Na, K, Ca, Mg or $NH_nR_{(4-n)}$ wherein R is an alkyl or substituted alkyl and n is 0 to 4. Preferred substituted alkyls include hydroxy alkyls. More preferred is hydroxyethyl. Preferred is wherein the substituted alkyl is $CH_2CH_2OH$ and n is 3. Preferably X' is X, X is $CH_2CH_2OA$, and A is $CF_2CFHO$—$R_f$.

The above compound of Formula I is a fluorinated sulfonate surfactant which lowers surface tension at very low concentration. Surface tension values in water are less than about 25 milli-newtons per meter, preferably less than about 20 milli-newtons per meter, at a concentration of surfactant in the water of less than about 0.1% by weight preferably less than about 0.01% by weight. The surfactant is characterized by its efficiency in lowering the surface tension at low concentrations by selective adsorption on the interface, which is determined by the amphiphilic nature of the surfactants. The term "amphiphilic" means attraction to two different kinds of media. The surfactants comprise a water-soluble hydrophilic part and a water-insoluble hydrophobic part.

The compound of the present invention, represented by Formula I comprises at least one hydrophobic part which contains the $R_f$ perfluoroalkyl group. As a result, the compound represented by Formula I of the present invention is able to lower surface tension at very low concentration. Having one or both of the hydrophobic parts as $R_f$ perfluoroalkyl group(s), the compound represented by Formula I of the present invention exhibits various levels of hydrophobic and oleophobic properties. Therefore, Formula I is suitable for providing improved surface effects including blocking resistance, enhanced hiding power (leveling), spreading, wettability, penetrability, foam inhibition and dispersibility. The improved surface effects by the compounds of the present invention are suitable for many industrial applications including aqueous coatings such as inks, paints, varnishes, and the like.

The compound represented by Formula I also comprises a hydrophilic part which contains sulfonic acid, or a salt of the acid. The hydrophilic part provides effective solubility in water media, and therefore the compounds represented by Formula I of the present invention exhibit surfactant properties. The compounds represented by Formula I are fluorinated sulfonate surfactant.

The above compound is prepared by reacting a perfluoro alkyl vinyl ether with a sulfonic acid, or a salt of sulfonic acid which contains at least one hydroxyl group in the presence of a strong base. When the reactant is a sulfonic acid salt, only a catalytic amount of base is required, typically about 10-20 mole % relative to the sulfonic acid salt. When the reactant is a sulfonic acid, enough base must be added so a catalytic amount of base remains after complete conversion of the sulfonic acid to the sulfonic acid salt, typically 110-120 mole % relative to the sulfonic acid. The base must be sufficiently reactive to deprotonate the hydroxy group to generate the alkoxide anion. Suitable bases include but are not limited to NaH, KH, sodium amide, lithium amide, potassium tert-butoxide, and KOH.

Examples of suitable sulfonic acids, or salts of sulfonic acids, which contain at least one hydroxyl group include $(HOCH_2CH_2)_2$—$NCH_2CH(OH)CH_2SO_3H$, $HOC(CH_3)_2$—$NHCH_2CH(OH)CH_2SO_3H$, $(HOCH_2CH_2)_2$—$NCH_2CH_2SO_3H$, $(HOCH_2CH_2)_2$—$NSO_3K$, $(HOCH_2CH_2)_2$—$NCH_2SO_3K$, $HOCH_2CH_2$—$N$—$(CH_2CH_2)_2$—$N$—$CH_2CH_2SO_3H$, $HOCH_2CH_2$—$N$—$(CH_2CH_2)_2$—$N$—$CH_2CH_2CH_2SO_3H$, $HOCH_2CH_2$—$N$—$(CH_2CH_2)_2$—$N$—$CH_2(OH)CH_2SO_3H$, $O$—$(CH_2CH_2)_2$—$N$—$CH_2(OH)CH_2SO_3H$, $(HOCH_2)_3C$—$NHCH_2CH(OH)CH_2SO_3H$, and $(HOCH_2)_3C$—$NHCH_2CH_2SO_3H$. Many of these sulfonic acids, or salts of sulfonic acids described above are commercially available from Sigma-Aldrich, Milwaukee, Wis. Other suitable sulfonic acids containing hydroxyl groups are well known in the literature. For example, some tertiary amines containing hydroxyl groups and sulfonic acid groups are suitable for use herein, such as 4-[bis-(2-hydroxyethane)-amino]-butanesulfonic acid, 3-morpholino-2-hydroxypropanesulfonic acid (MOPSO), N-(2-hydroxyethyl)piperazine-N'-3-propanesulfonic acid (EPPS); N-(2-hydroxyethyl) piperazine-N'-3-ethanesulfonic acid (BES), piperazine-N-2-hydroxyethane-N'-3-methylpropanoate, N-tris(hydroxymethyl)methyl-2-aminoethane sulfonic acid (TES), 1,3-bis[tris(hydroxymethyl)methylamino]propane(bis-Tris propane), piperazine-N,N'-bis(2-hydroxypropane)sulfonic acid (POPSO) and 2-hydroxy-3-[4-(2-hydroxyethyl)piperazin-1-yl]propane-1-sulfonic acid (HEPPSO) as cited in U.S. Pat. No. 6,919,173.

Generally the perfluoroalkyl vinyl ether is slowly added to the sulfonic acid, or salt thereof, in the presence of base, in solvent using means to control the resulting temperature increase. Suitable solvents include dimethylformamide, dimethyl acetamide, dimethyl sulfoxide (DMSO), N-methylpyrrolidinone, hexamethylphosphoramide, and similar solvents one skilled in the art would choose based on the properties of the starting materials, reaction products, and methods for product purification. The reaction is typically permitted to continue for several hours. At completion of the reaction the solvent is removed at ambient temperature to prevent product degradation.

There are various methods for making the fluorinated vinyl ether which is used in the above reaction. These methods include making fluorinated vinyl ethers by reacting a 2-alkoxypropionyl fluoride in a stationary bed of a metal carbonate, a tubular reactor filed with dried metal carbonate and equipped with a screw blade running through the tube, and a fluidized bed of metal carbonate. US Patent Application 2007/0004938 describes a process to produce fluorinated vinyl ethers by reacting a 2-alkoxypropionyl fluoride with a metal carbonate under anhydrous conditions in a stirred bed reactor at a temperature above the decarboxylation temperature of an intermediate carboxylate to produce fluorinated vinyl ether. Examples of fluorinated vinyl ethers suitable for use in the present invention include $CF_3$—$O$—$CF$=$CF_2$, $CF_3CF_2$—$O$—$CF$=$CF_2$, $CF_3CF_2CF_2$—$O$—$CF$=$CF_2$, and $CF_3CF_2CF_2CF_2$—$O$—$CF$=$CF_2$, which are available from E. I. du Pont de Nemours and Company, Wilmington, Del.

The product of the reaction is a fluorinated sulfonate surfactant which lowers surface tension and provides improved surface effects such as blocking resistance, enhanced hiding power (leveling), spreading, wettability, penetrability, foam inhibition, dispersibility, and water and oil repellency. These improved surface effects are advantageous in many industrial applications including aqueous coatings such as inks, paints, varnishes, and the like.

The present invention further comprises a method of lowering surface tension of a medium, typically a liquid, comprising adding to the medium a compound of Formula I as described above. The surfactants of Formula I of the present invention are effective in lowering the surface tension of a wide variety of media. Examples of suitable medium include, for example, a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium. These surfactants are especially suitable for lowering the surface tension of water, aqueous solutions, and aqueous emulsions. A low concentration of less than about 0.01% by weight of a compound of Formula I in the liquid is effective. The amphoteric nature of the surfactant of Formula I of the present invention results in it being effective across a broad pH range. Preferably the pH is greater than about 4.

The present invention further comprises a method of altering the surface behavior of a liquid comprising adding to the liquid a compound of Formula I as defined above. A wide variety of surface behaviors is included. Examples are wetting, penetration, spreading, leveling, flowing emulsification, stabilizing and dispersion in the wet liquids. Other examples include antiblocking, repellency and releasing in a dried coating composition on a treated substrate. Consequently, the surfactants of Formula I are useful in a wide variety of end use applications.

The compound of Formula I of the present invention is suitable for the use in coatings, paint, pigment, varnishes, finishing agents, floor waxes or finishes, inks and dyes. Surface effects provided include enhanced hiding power, leveling, antiblocking, anticratering, control of soiling, water and oil repellency, wetting, dispersion, blocking resistance, color development, and to combat pigment flotation problems.

Particular coating compositions suitable for use with the surfactants of the present invention, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. 1, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Blocking is the undesirable sticking together of two coated surfaces when pressed together, or placed in contact with each other for an extended period of time. When blocking occurs separation of the surfaces can result in disruption of the coating on one or both surfaces. Thus improved resistance to blocking is beneficial in many situations where two coated surfaces need to be in contact, for example on window frames.

When used as additives to a coating base the compositions of the present invention of Formula (I) as defined above are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about from about 0.01 weight % to about 1 weight %, and more preferably from about 0.1 weight % to about 0.5 weight % is used.

Floor waxes, polishes, or finishes (hereinafter "floor finishes") are generally water based or solvent based polymer emulsions. The surfactants of Formula I of the present invention are suitable for use in such floor finishes. Commercially available floor finish compositions typically are aqueous emulsion-based polymer compositions comprising one or more organic solvents, plasticizers, coating aides, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly(alkyl methacrylates). Commercially available acrylic copolymers used in floor finishes include, for example, methyl methacrylate/butyl acrylate/methacrylic acid (MMA/BA/MAA) copolymers; methyl methacrylate/butyl acrylate/acrylic acid (MMA/BA/A) copolymers, and the like. Commercially available styrene-acrylic copolymers include styrene/methyl methacrylate/butyl acrylate/methacrylic acid (S/MMA/BA/MMA) copolymers; styrene/methyl methacrylate/butyl acrylate/acrylic acid (S/MMA/BA/M) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenated coconut oil or soybean oil, and the mineral waxes such as paraffin or ceresin. The waxes typically range from 0 to about 15 weight percent and preferably from about 2 to about 10 weight percent based on the weight of the finish composition.

When used as additives to a floor finish the compositions of the present invention of Formula (I) as defined above are effectively introduced to the composition by thoroughly stirring it in at room or ambient temperature. More elaborate mixing can be employed such as using a mechanical shaker or providing heat or other methods. When used as an additive to floor finishes, the compositions of the invention generally are added at about 0.001 weight % to about 5 weight % by dry weight of the composition of the invention in the wet composition. Preferably about from about 0.01 weight % to about 1 weight %, and more preferably from about 0.1 weight % to about 0.5 weight % is used.

The compounds of Formula I are useful in many additional applications. Examples of some applications include the following.

The compounds represented by Formula I of the present invention are suitable for the use in fire fighting compositions, for example as a wetting agent, emulsifying agent and/or dispersion. They are also useful as a component in aqueous film forming extinguishing agents, as an additive to dry chemical extinguishing agents in aerosol-type extinguishers, and as a wetting agent for sprinkler water.

The compounds represented by Formula I of the present invention are suitable for the use in agricultural compositions. Examples include as a wetting agent, emulsifying agent and/or dispersion agent for herbicides, fungicides, weed killers, parasiticides, insecticides, germicides, bactericides, nematocides, microbiocides, defolients, fertilizers and hormone growth regulators. Formula I compounds are also suitable as wetting agent for foliage, for live stock dips and to wet live stock skins; as an ingredient in sanitizing, discoloring and cleaning compositions; and in insect repellent compositions. The compounds of Formula I are also useful as a wetting agent, emulsifying agent and/or dispersion agent in the manufacture of paper and plywood veneer. The compounds of Formula I are also suitable as grease/oil repellents for paper, wood, leather, skins, metals, textiles, stone, and tiles, and as penetrant for preservative impregnation.

The compounds represented by Formula I of the present invention are also suitable for the use as a wetting agent, emulsifying agent and/or dispersion agent for polymerization reactions, particularly polymerization of fluoromonomers. These compounds are also suitable as a latex stabilizer; as an additive for foam applications to control spreading, crawling and edge buildup; and as foaming agents, mold release agents or demolding agents; as internal antistatic agent and anti-blocking agent for polyolefins; as a flow modifier for extruding hot melts to aid in the control of spreading, uniformity, anticratering; and as retarder for plasticizer migration or evaporation in the plastics and rubber industry.

The compounds represented by Formula I of the present invention are further suitable for the use in the petroleum industry as a wetting agent for oil well treatments and drilling mud; as a film evaporation inhibitor for gasoline, jet fuel, solvents, hydrocarbons; as a lubricant or cutting oil improver to improve penetration times; as an oil spill collecting agent; and as an additive to improve tertiary oil well recovery.

The compound represented by Formula I of the present invention are further suitable for use in the textile and leather industries as a wetting agent, antifoaming agent, penetrating agent or emulsifying agent; or as a lubricant for textiles, nonwoven fabrics and leather treatment; for fiber finishes for spreading, and uniformity; as a wetting agent for dyeing; as a binder in nonwoven fabrics; and as a penetration additive for bleaches.

The compounds represented by Formula I of the present invention are further suitable for the use in the mining and metal working industries, in the pharmaceutical industry, automotives, building maintenance and cleaning, in household, cosmetic and personal products, and in photography and graphic arts to provide improved surface effects.

TEST METHODS

The following test methods are used in the Examples herein.

Test Method 1—Surface Tension

The surface tension of each sample was measured in accordance with the following procedure. An aliquot (30 mL) of each aqueous solution containing a sample to be tested was poured into separate glass dishes and allowed to equilibrate for 20-30 seconds before measurements were taken. The measurements were conducted using a Krüss K11 tensiometer (available from Krüss GmbH, Hamburg, Germany) using the 'Wilhelmy Plate Method' wherein a small platinum plate with a roughened surface was suspended perpendicular to the liquid surface contained in the glass dish. The plate was attached to a force measuring balance. The glass dish was raised manually until the surface of the liquid was a few millimeters in distance from the suspended plate. The dish was then raised electronically and the wetting of the plate provided for a force proportional to the surface tension of the liquid. A mean surface tension value was obtained from ten consecutive readings and reported in units of milli-newtons/meter (mN/M). A lower value indicates superior performance.

Test Method 2—Leveling Effect in Floor Finishes (Waxes)

To test the performance of samples in their wetting and leveling ability, the samples were added to a floor polish RHOPLEX 3829, Formulation N-29-1, which is available from Rohm and Haas Company, Philadelphia, Pa., and applied to half of a stripped 12 inch×12 inch (30.36 cm×30.36 cm) vinyl tile. A 1% (active ingredient basis) solution of the surfactant to be tested was prepared by dilution in deionized water. Following the resin manufacturer protocols, a 100 g portion of the RHOPLEX 3829 formulation was prepared, followed by addition of 0.75 g of the 1% (active ingredient basis) surfactant solution, to provide a test floor polish.

The test floor polish was applied to the tile by placing a 3 mL portion of the test polish in the center of the tile, and spreading from top to bottom using an applicator, and finally placing a large "X" across the tile, using the applicator. The tile was allowed to dry for 30 min and a total of 5 coats were applied. After each coat, the tile was rated on a 1 to 5 scale (1 being the worst, 5 the best) on the surfactant's ability to promote wetting and leveling of the polish on the tile surface. The rating is determined based on comparison of a tile treated with the floor polish that contained no fluorosurfactant with a higher rating indicating superior performance.

Subjective Tile Rating Scale

1 Uneven surface coverage of the film, significant streaking and surface defects 2 Visible streaking and surface defects, withdrawal of the film from the edges of the tile 3 Numerous surface defects and streaks are evident but, generally, film coats entire tile surface 4 Minor surface imperfections or streaking 5 No visible surface defects or streaks.

Test Method 3—Blocking Resistance in Semi-Gloss Latex Paint

The blocking resistance of paints was measured according to a slightly amended version of an ASTM method (D 4946-89). This test method describes an accelerated procedure for evaluating the face-to-face blocking resistance of commercial architectural paints and the paints which contained the compound of the Formula I of the present invention. Blocking, for the purpose of this test, is defined as the undesirable sticking together of two painted surfaces when pressed together or placed in contact with each other for an extended period of time. The paint to be tested was cast on a polyester test panel using an applicator blade. The coated panels were conditioned in a room which was maintained at 18 to 29° C. and 40-60% relative humidity for 24 hours. After the panels were conditioned for 24 hours, six squares (3.8 cm square) were cut from the painted test panel. The cut sections (three pairs) were positioned with the painted surfaces face-to-face for each of the paints to be tested, and a pressure of about 1.8 psi (127 g/cm2) was applied. The paint films were placed in an oven for 30 minutes at 50° C. to increase the severity of the test. After cooling, the panels were peeled apart. The degree of blocking was measured on a subjective scale for tack or seal, using a series of descriptive terms corresponding to numerical ASTM values from 0 to 10. The rating system is described in the Table 1. The degree of seal was estimated from the appearance of the specimens; the fraction of the paint surfaces that adhered, or where paint tore away from the test panel backing was an indication of seal.

TABLE 1

| Blocking Resistance Numerical Ratings | Description of the Separation | Performance Description |
|---|---|---|
| 10 | no tack | perfect |
| 9 | trace tack | excellent |
| 8 | very slight tack | very good |
| 7 | slight tack | good/very good |
| 6 | moderate to slight tack | good |
| 5 | moderate tack | fair |
| 4 | very tacky - no seal | poor to fair |
| 3 | 5 to 25% seal | poor |
| 2 | 25 to 50% seal | poor |
| 1 | 50 to 75% seal | very poor |
| 0 | 75 to 100% seal | very poor |

Test Method 4—Hiding Power (Leveling) in Semi-Gloss Latex Paint

The hiding power (leveling) of paints was measured according to a slightly amended version of the standard method, ASTM D2805-96a. This test method describes a procedure for evaluating the Hiding Power of architectural paint films via use of a Contrast Ratio, the photometric measure of the film opacity, or hiding. Hiding Power was defined as the Spreading Rate required for full hiding over a standard black and white substrate. The latter was defined in to have CIE-Y reflectances of 0.01 (1%) max. and 0.80 (80%) respectively. This method determined the Contrast Ratio using a specified film thickness for sample to sample comparison. Reflectometry measurement was performed using the Minolta Chroma Meter CR-200. The CIE color space (Y, y, x) was used, particularly the Y-tristimulus value. Polyester scrube test panels (Leneta "Opacity" or "Penopac" charts or the equivalent BYK-Gardner charts) were used.

The paint to be tested was evenly cast on the Opacity test chart using an applicator blade. 2 or 3 mil applicator blades can be used, but the film thickness must be equal for all samples tested. The photometric Contrast Ratio for the Control sample is less than 0.98, which was visually just short of total extinction of contrast. The coated charts were conditioned at room temperature for the desired period of time (no less than 40 hours). All painted charts were protected from surface contamination including grease, oil, fingerprints, dust, et cetera. The painted chart was placed on a level bench or platform. Using the reflectometer, the CIE tristimulus measurement mode was chosen. The Y-tristimulus value was measured and recorded in triplicate across different areas of the painted "black" portion of the chart. These values were averaged to obtain $R_0$ where $R_0$=reflectance over black substrate. The measuring and recording were repeated over the painted "white" portion of the chart. These values were averaged to obtain $R_{0.80}$ where $R_{0.80}$=reflectance over white substrate. $R_{0.80}$ is also referred to as $R_W$ in literature. The Contrast Ratio (C) was determined using the formula $C=R_0/R_{0.80}$. Contrast Ratios were graphically compared to one another for samples of the same wet film thickness. A higher Contrast Ratio indicates superior performance.

EXAMPLES

Example 1

BES Sodium salt, (N,N-bis(2-hydroxyethyl)-2-aminoethanesulphonic acid, sodium salt), was obtained from Sigma-Aldrich, Milwaukee, Wis. It was dried in a vacuum oven at 110° C. for 48 hours. Perfluoropropyl vinyl ether (perfluoropropyl vinyl ether) available from E. I. du Pont de Nemours and Company, Wilmington, Del. was used in the preparation.

A 500 mL 4-neck flask was charged in a nitrogen filled glove box with BES Sodium salt (11.75 g, 0.05 mole), 200 mL anhydrous DMF, and NaH (0.24 g, 0.01 mole). The flask was removed from the drybox and connected to a positive pressure nitrogen line with a bubbler. An addition funnel containing perfluoropropyl vinyl ether (29.3 g, 0.11 mole) was connected to the flask under nitrogen purge. The mixture was stirred vigorously by magnetic stirring and the perfluoropropyl vinyl ether was added dropwise. The reaction was exothermic. The reaction mixture was maintained at room temperature or slightly higher by slow addition of the perfluoropropyl vinyl ether and use of a water/ice bath for cooling. At the end of the perfluoropropyl vinyl ether addition, the mixture was allowed to stand for 16 hours at room temperature and then filtered to remove a small amount of solids. The solvents were removed from the filtrate in vacuo on a rotary evaporator at room temperature. Room temperature removal of solvent was essential. Heating to increase the rate of solvent removal was found to result in decomposition of the product. The sticky product was dissolved in 50 mL of acetone and precipitated by addition to 500 mL of hexane. The solution was decanted from the product and repeated washing with hexane followed by room temperature drying at high vacuum was necessary to remove all of the DMF. 22.5 g (light yellow solid, 61% yield) of product was obtained of $(CF_3CF_2CF_2OCFHCF_2OCH_2CH_2)_2NCH_2CH_2SO_3^-Na^+$. $^1H$ NMR ($d_6$-acetone): 2.93 (NC$\underline{H}_2$CH$_2$O), 3.09 (NC$\underline{H}_2$C$\underline{H}_2$SO$_3$), 4.10 (NCH$_2$C$\underline{H}_2$O), 6.53 (d, J=40 Hz, CFH).

This product of Example 1 was dissolved in water at weight percents of 0.1% and 0.01%, and the surface tension measured in accordance with test Method 1. The results are in Table 2.

TABLE 2

| Example | Surface Tension, mN/M 0.1 wt % | Surface Tension, mN/M 0.01 wt % |
|---|---|---|
| 1 | 15.7 | 18.4 |

The data in Table 2 shows that Example 1 was effective, at very low concentrations, to lower the surface tension of water from it usual level of 72.8 mN/M at 20° C.

Example 1 was mixed with a non-fluorinated surfactant. The comparative non-fluorinated surfactant was alkyldiphenyloxide disulfonate (DOWFAX 2A1), which is anionic surfactant and available from Dow Chemical Company, Midland, Mich. The aqueous solution of a mixture of Example 1 and alkyldiphenyloxide disulfonate (DOWFAX 2A1) contained, at combined weight percent, 0.1%, and the aqueous solution of alkyldiphenyloxide disulfonate (DOWFAX 2A1) contained 0.1% weight percent. Each was tested for surface tension in accordance with Test Method 1. The results are in Table 3.

TABLE 3

| Surfactant Mixture | Surface Tension mN/M |
|---|---|
| 0.05 wt % Example 1 + 0.05 wt % DOWFAX 2A1 | 15.4 |
| 0.1 wt % DOWFAX 2A1 | 35.7 |

The data in Table 3 shows that the mixture containing Example 1 had a lower surface tension than the non-fluorinated surfactant alone.

Example 1 was added, at a level of 0.75% by weight, to a floor polish RHOPLEX 3829, Formulation N-29-1, which is available from Rohm and Haas Company, Philadelphia, Pa. After mixing, the wetting and leveling ability of the floor polish, with and without Example 1, was tested in accordance with Test Method 2. The results are in Table 4.

TABLE 4

Leveling Effect in Floor Finish

| Coating | 0.75 wt % Example 1 + floor polish | Control floor polish |
|---|---|---|
| $1^{st}$ | 3 | 2 |
| $2^{nd}$ | 5 | 2 |
| $3^{rd}$ | 4+ | 1 |
| $4^{th}$ | 5 | 1 |
| $5^{th}$ | 4 | 1 |

The data in Table 4 shows that the addition of Example 1 to the floor polish increased the leveling effect.

Example 1, at a level of 0.1% by weight, was added to a semi-gloss acrylic latex paint from Vista Paint Corporation, Fullerton, Calif., with 2% propylene glycol added. After mixing, the blocking resistance of the paint, with and without Example 1, was tested on polyester panels in accordance with Test Method 3. The results are in Table 5.

TABLE 5

Blocking Resistance in Semi-Gloss Latex Paint

| Rating | Rating |
|---|---|
| 0.1 wt % Example 1 + latex paint | 9.3 |
| Control latex paint | 4.8 |

The data in Table 5 shows addition of Example 1 to the paint increased resistance to blocking.

Example 1, at a level of 0.1% by weight, was added to a semi-gloss acrylic latex paint from Vista Paint Corporation, Fullerton, Calif., with 2% propylene glycol added. The hiding power of the paint, with and without Example 1, was tested in accordance with Test Method 4. The results are in Table 6.

TABLE 6

Hiding Power in Semi-Gloss Latex Paint

| Rating | Contrast Ratio |
|---|---|
| 0.1 wt % Example 1 + latex paint | 99% |
| Control latex paint | 93% |

The data in Table 6 shows addition of Example 1 to the paint increased its hiding power.

Example 2

The compound of Example 1 (10.0 g, 0.013 mole) was dissolved in 200 mL distilled water and acidified with 15 mL of 37% aqueous HCl. Solid material precipitated from the aqueous solution. The heterogeneous mixture was washed with 2×400 mL methylene chloride. During the washes the insoluble material was located primarily at the phase boundary. The clear portion of the lower methylene chloride layer was removed. Acetone (20 mL) was added to the heterogeneous mixture and it then formed two separated homogeneous phases. The bottom layer was drawn off and the solvents were removed in vacuo to give 8.1 g light yellow solid (83% yield) product $(CF_3CF_2CF_2OCFHCF_2OCH_2CH_2)_2N^+(H)CH_2CH_2SO_3^-$. The product was insoluble in water and methylene chloride and soluble in acetone. $^1H$ NMR was consistent with the protonated zwitterion ($d_6$-acetone): 3.06 (t, $NCH_2\underline{CH}_2SO_3^-$), 3.86 (t, $N\underline{CH}_2CH_2SO_3^-$), 3.95 (t, $NCH_2\underline{CH}_2O$), 4.62 (t, $N\underline{CH}_2CH_2O$), 6.84 (d, CHF, $J_{HF}=52$ Hz).

Example 3

The compound of Example 2 (0.71 g, 0.95 mmol) was dissolve in 10 mL of methanol and triethanolamine (0.15 g, 1.00 mmol) was added. The mixture was stirred for 1 h, and then the methanol was removed in vacuo on a rotary evaporator to give 0.90 g light yellow oil product $[(CF_3CF_2CF_2OCFHCF_2OCH_2CH_2)_2NCH_2CH_2SO_3]^-[HN(CH_2CH_2OH)_3]^+$. $^1H$ NMR ($d_6$-acetone) was consistent with complete conversion to the $[HN(CH_2CH_2OH)_3]^+$ salt. There were no peaks detected for free triethanolamine, however the integrals of the peaks assigned to the cation $[HN(CH_2CH_2OH)_3]^+$ were slightly high, probably due to rapid exchange of the proton between the cation and the slight excess of triethanol amine leading to peak averaging: 2.92 (m, $NCH_2\underline{CH}_2SO_3^-$, $N\underline{CH}_2CH_2O$), 3.04 (m, $N\underline{CH}_2CH_2SO_3^-$), 3.32 (m, $[HN(\underline{CH}_2CH_2OH)_3]^+$), 3.87 (m, $[HN(CH_2C\underline{H}_2OH)_3]^+$), 4.10 (t, $NCH_2\underline{CH}_2O$), 6.64 (d, CHF, $J_{HF}=44$ Hz).

This product was dissolved in water at weight percents of 0.1% and 0.01%, and the surface tension measured in accordance with test Method 1. The results are in Table 7.

TABLE 7

| Example | Surface Tension, mN/M 0.1 wt % | Surface Tension, mN/M 0.01 wt % |
| --- | --- | --- |
| 3 | 15.9 | 15.8 |

The data in Table 7 shows that Example 3 was effective, at a very low concentration, to lower the surface tension of water from its usual level of 72.8 mN/M at 20° C.

What is claimed is:
1. A compound of Formula I,

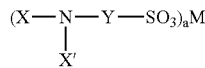

Formula I wherein
Y is a bond or $C_mH_{2m-p}(OA)_p$ wherein m is 0 to 4, and p is 0 or 1,
X' is X or H,
X is $CH_2CH_2OA$, $CH(CH_2OA)_2$, $C(CH_2OA)_3$, or
X and X' combine to form $(CH_2CH_2)_2NCH_2CH_2OA$ or $(CH_2CH_2)_2O$, provided that when X and X' combine to form $(CH_2CH_2)_2O$ then Y is $CH_2CH(OA)CH_2$,
A is $CF_2CFHO$—$R_f$ or H,
$R_f$ is $C_nF_{2n+1}$ wherein n is an integer of 1 to about 6,
M is a cation having a charge equal to a, and
a is a positive integer equal to 1 or 2,
provided that at least one of X, X', or Y contains A equal to $CF2CFHO$—$R_f$.
2. The compound of claim 1 wherein $R_f$ is $C_3F_7$ or $C_4F_9$.
3. The compound of claim 1 wherein M is Na, K, Ca, Mg or $NH_nR_{(4-n)}$ wherein R is an alkyl or substituted alkyl and n is 0 to 4.
4. The compound of claim 3 wherein the substituted alkyl is $CH_2CH_2OH$ and n is 3.
5. The compound of claim 3 wherein M is Na.
6. The compound of claim 1 wherein X' is X, X is $CH_2CH_2OA$, and A is $CF_2CFHO$—$R_f$.
7. The compound of claim 4 wherein Y is $CH_2CH_2$.
8. A composition comprising the compound of claim 1, in an aqueous solution, emulsion or dispersion.
9. The compound of claim 1, having a surface tension of less than about 25 mN/M at a concentration of 0.1% by weight in water.
10. The compound of claim 1, having a surface tension of less than about 20 mN/M at a concentration of 0.1% by weight in water.
11. A composition comprising the compound of claim 1, a non-fluorinated surfactant or a fluorinated surfactant.
12. A method of altering the surface behavior of a liquid comprising adding to the liquid a compound of claim 1 or a mixture thereof.
13. The method of claim 12 wherein the altering the surface behavior is lowering the surface tension.
14. The method of claim 12 wherein the surface behavior is selected from the group consisting of wetting, penetrating, spreading, leveling, flowing, emulsifying, dispersing, repelling, releasing, lubricating, etching, bonding, and stabilizing.
15. The method of claim 12 wherein the liquid is coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, floor finish, or bonding agent.
16. The method of claim 15 wherein the liquid is a coating composition.
17. The method of claim 16 wherein the surface behavior is resistance to blocking in the coating composition after drying.
18. The method of claim 16 wherein the surface behavior is wetting and leveling during application of the coating composition to a surface.
19. The method of claim 15 wherein the liquid is a floor finish.
20. The method of claim 19 wherein the surface behavior is leveling.

* * * * *

UNITED STATES PATENT AND TRADEMARK OFFICE
CERTIFICATE OF CORRECTION

PATENT NO. : 7,399,887 B1
APPLICATION NO. : 11/890374
DATED : July 15, 2008
INVENTOR(S) : Peter Michael Murphy et al.

It is certified that error appears in the above-identified patent and that said Letters Patent is hereby corrected as shown below:

Claim 1, col. 14 line 14, "CF2CFHO-R$_f$" should read -- CF$_2$CFHO-R$_f$ --.

Signed and Sealed this

Sixteenth Day of December, 2008

JON W. DUDAS
*Director of the United States Patent and Trademark Office*